(12) United States Patent
Criscito

(10) Patent No.: US 9,370,545 B2
(45) Date of Patent: Jun. 21, 2016

(54) METHODS AND COMPOUNDS FOR INTENSIVE SKIN REPAIR AND HEALING INCLUDING ACTIVE ORGANIC AND SYNTHETIC COMPOUNDS

(71) Applicant: Desert Harvest, Hillsborough, NC (US)

(72) Inventor: Pat Criscito, Hurdle Mills, NC (US)

(73) Assignee: DESERT HARVEST, Hillsborough, NC (US)

( * ) Notice: Subject to any disclaimer, the term of this patent is extended or adjusted under 35 U.S.C. 154(b) by 14 days.

(21) Appl. No.: 14/470,253

(22) Filed: Aug. 27, 2014

(65) Prior Publication Data

US 2016/0058820 A1    Mar. 3, 2016

(51) Int. Cl.
*A61K 36/00* (2006.01)
*A61K 36/886* (2006.01)
*A61K 31/16* (2006.01)

(52) U.S. Cl.
CPC ............... *A61K 36/886* (2013.01); *A61K 31/16* (2013.01)

(58) Field of Classification Search
None
See application file for complete search history.

(56) References Cited

U.S. PATENT DOCUMENTS 5,711,935 A * 1/1998 Hill et al. .................... 424/49

* cited by examiner

*Primary Examiner* — Qiuwen Mi
(74) *Attorney, Agent, or Firm* — Lathrop & Gage LLP

(57) ABSTRACT

A skin treatment compound includes Lidocaine and *aloe vera*. The *aloe vera* is *Barbadensis* Miller species. Optionally, the skin treatment compound includes *Calendula*. Alternatively, the skin treatment compound includes natural preservatives. Optionally, the natural preservatives include *Leuconostoc*/Radish Root Ferment Filtrate, *Lonicera Japonica* (Honeysuckle) Flower Extract, *Lonicera Caprifolium* (Honeysuckle) Extract, *Populus Tremuloides* (Aspen) Bark Extract, and Gluconolactone.

10 Claims, 4 Drawing Sheets

METHODS AND COMPOUNDS FOR INTENSIVE SKIN REPAIR AND HEALING INCLUDING ACTIVE ORGANIC AND SYNTHETIC COMPOUNDS

TECHNICAL FIELD

The embodiments described herein include compounds and methods of application for relief from irritation and pain from cancer radiation treatments, shingles, tattoos, neuropathy, first and second degree burns, and many other ailments.

BACKGROUND

Skin irritation in individuals is common, especially those undergoing cancer radiation treatments, as well as dealing with burns or other maladies. Relieving the pain and speeding the healing of such irritations is important to individuals. For health reasons, such individuals many times desire a primarily organic solution for aiding in the healing of such skin irritations.

SUMMARY

Embodiments of the compounds and methods described herein aid in skin repair and relieve irritation and pain that may result from various treatments including radiation, shingles, tattoos and tattoo removal, and neuropathy, among other ailments.

In one embodiment, a method for making a skin treatment compound includes making a Phase A portion of the skin treatment compound including: mixing Ultrez powder with water to wet the Ultrez powder; adding glycerin; and heating and holding the Phase A portion at 170° F. Ultrez polymer is a hydrophobically modified cross-linked acrylate copolymer (Acrylates/C10-30 Alkyl Acrylate Crosspolymer). The method further includes making a Phase B portion of the skin treatment compound including: adding lubricants; heating the Phase B portion at 170° F.; stirring the Phase B portion; and resting the Phase B portion for ten minutes. The method further includes mixing the Phase B portion with the Phase A portion. The method further includes adding sodium hydroxide to the Phase B portion with the Phase A portion to form a Phase C portion. The method further includes making a Phase E portion of the skin treatment compound including: dissolving Vitamin C and Lidocaine in water; adding a Phase D portion with Japanese Green Tea Extract, Aloe Vera Powder, and natural preservatives; and adding the Phase C portion. The method further includes mixing the resulting skin treatment compound. Optionally, the lubricants include at least one ingredient selected from a list consisting of Glyceryl Stearate, Stearic Acid, Cetyl Alcohol, Hi Oleic Safflower Oil, Rosehip Seed Oil, Vitamin E, and Chia Seed Oil. Alternatively, the lubricants include Glyceryl Stearate, Stearic Acid, Cetyl Alcohol, Hi Oleic Safflower Oil, Rosehip Seed Oil, Vitamin E, and Chia Seed Oil. Optionally, the Phase D portion includes at least one botanical selected from a list consisting of *Chamomilla Recutita (Matricaria)* Extract, *Calendula Officinalis (Calendula)* Flower Extract, *Anthemis Nobilis* (Roman Chamomile) Flower Extract, *Centaurea Cyanus* (Cornflower) Flower Extract, *Tilia Cordata* (Linden) Flower Extract, *Hypericum Perforatum* (St. John's Wort) Extract, *Vitis Vinifera* (Grapeseed) Extract, *Tabebuia Impetiginosa* (Pau d'Arco) Extract, and *Thymus Vulgaris* (Thyme) Oil Extract. Alternatively, the Phase D portion includes *Chamomilla Recutita (Matricaria)* Extract, *Calendula Officinalis (Calendula)* Flower Extract, *Anthemis Nobilis* (Roman Chamomile) Flower Extract, *Centaurea Cyanus* (Cornflower) Flower Extract, *Tilia Cordata* (Linden) Flower Extract, *Hypericum Perforatum* (St. John's Wort) Extract, *Vitis Vinifera* (Grapeseed) Extract, *Tabebuia Impetiginosa* (Pau d'Arco) Extract, and *Thymus Vulgaris* (Thyme) Oil Extract. Optionally, the natural preservatives include *Leuconostoc*/Radish Root Ferment Filtrate, *Lonicera Japonica* (Honeysuckle) Flower Extract, *Lonicera Caprifolium* (Honeysuckle) Extract, *Populus Tremuloides* (Aspen) Bark Extract, and Gluconolactone. In one alternative, the method further includes adjusting a pH of the skin treatment compound to between 6.8 and 7.2. In one alternative, the method further includes adjusting a viscosity of the skin treatment compound to between 35,000 and 45,000 centipoise (cps) at 25° C.

In one embodiment, a skin treatment compound includes water; Ultrez powder; glycerin; skin healing botanicals; sodium hydroxide; Vitamin C; Lidocaine; a Phase D portion; Japanese Green Tea Extract; *Aloe Vera* Powder; and natural preservatives. Optionally, the lubricating ingredients include at least one ingredient selected from a list consisting of Glyceryl Stearate, Stearic Acid, Cetyl Alcohol, Hi Oleic Safflower Oil, Rosehip Seed Oil, Vitamin E, and Chia Seed Oil. Alternatively, the lubricating ingredients include Glyceryl Stearate, Stearic Acid, Cetyl Alcohol, Hi Oleic Safflower Oil, Rosehip Seed Oil, Vitamin E, and Chia Seed Oil. In one alternative, the Phase D portion includes at least one botanical selected from a list consisting of *Chamomilla Recutita (Matricaria)* Extract, *Calendula Officinalis (Calendula)* Flower Extract, *Anthemis Nobilis* (Roman Chamomile) Flower Extract, *Centaurea Cyanus* (Cornflower) Flower Extract, *Tilia Cordata* (Linden) Flower Extract, *Hypericum Perforatum* (St. John's Wort) Extract, *Vitis Vinifera* (Grapeseed) Extract, *Tabebuia Impetiginosa* (Pau d'Arco) Extract, and *Thymus Vulgaris* (Thyme) Oil Extract. Optionally, the Phase D portion includes *Chamomilla Recutita (Matricaria)* Extract, *Calendula Officinalis (Calendula)* Flower Extract, *Anthemis Nobilis* (Roman Chamomile) Flower Extract, *Centaurea Cyanus* (Cornflower) Flower Extract, *Tilia Cordata* (Linden) Flower Extract, *Hypericum Perforatum* (St. John's Wort) Extract, *Vitis Vinifera* (Grapeseed) Extract, *Tabebuia Impetiginosa* (Pau d'Arco) Extract, and *Thymus Vulgaris* (Thyme) Oil Extract. Alternatively, the natural preservatives include *Leuconostoc*/Radish Root Ferment Filtrate, *Lonicera Japonica* (Honeysuckle) Flower Extract, *Lonicera Caprifolium* (Honeysuckle) Extract, *Populus Tremuloides* (Aspen) Bark Extract, and Gluconolactone. Optionally, the natural preservatives include at least one botanical selected from a list consisting of *Leuconostoc*/Radish Root Ferment Filtrate, *Lonicera Japonica* (Honeysuckle) Flower Extract, *Lonicera Caprifolium* (Honeysuckle) Extract, *Populus Tremuloides* (Aspen) Bark Extract, and Gluconolactone. Optionally, a pH of the skin treatment compound is between 6.8 and 7.2. Alternatively, a viscosity of the skin treatment compound is between 35,000 and 45,000 centipoise (cps) at 25° C.

In another embodiment, a skin treatment compound includes Lidocaine and *aloe vera*. The *aloe vera* is *Barbadensis* Miller species. Optionally, the skin treatment compound includes *Calendula*. Alternatively, the skin treatment compound includes natural preservatives. Optionally, the natural preservatives include *Leuconostoc*/Radish Root Ferment Filtrate, *Lonicera Japonica* (Honeysuckle) Flower Extract, *Lonicera Caprifolium* (Honeysuckle) Extract, *Populus Tremuloides* (Aspen) Bark Extract, and Gluconolactone. Alternatively, the natural preservatives include at least one botanical selected from a list consisting of *Leuconostoc*/Radish Root Ferment Filtrate, *Lonicera Japonica* (Honeysuckle)

Flower Extract, *Lonicera Caprifolium* (Honeysuckle) Extract, *Populus Tremuloides* (Aspen) Bark Extract, and Gluconolactone.

In another embodiment, a method of treating skin irritation includes treating the skin irritation with an effective amount of a compound. The compound includes Lidocaine and *aloe vera*. The *aloe vera* is *Barbadensis* Miller species. Optionally, the skin treatment compound includes *Calendula*. Alternatively, the skin treatment compound includes natural preservatives. Optionally, the natural preservatives include *Leuconostoc*/Radish Root Ferment Filtrate, *Lonicera Japonica* (Honeysuckle) Flower Extract, *Lonicera Caprifolium* (Honeysuckle) Extract, *Populus Tremuloides* (Aspen) Bark Extract, and Gluconolactone.

DETAILED DESCRIPTION OF THE PREFERRED EMBODIMENTS

Figure 1:
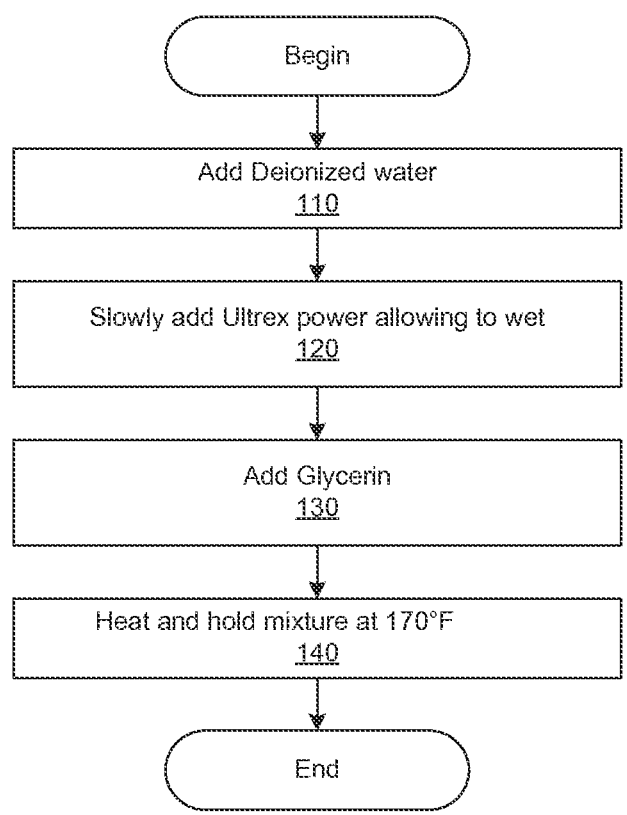
FIG. 1 shows an exemplary method of making Phase A of a compound for intensive skin repair and healing.

Embodiments of methods and compounds are described for skin repair and healing and relief from irritation and pain that may result from various treatments including radiation, shingles, tattoos and tattoo removal, neuropathy, or other skin-related issues, and are for illustrative purposes only. The term the "compound" is used repeatedly herein. The term "compound" generally refers to the various embodiments described herein that include in many embodiments a combination of ingredients including Lidocaine, *aloe vera* (in many cases *Barbadensis* Miller species), and *Calendula*, as well as a combination of many other ingredients, and the scope of the coverage of the claims is only intended to be limited by the specifics of the claims and not the examples described in relation to possible compounds. The compound typically is delivered in a cream or lotion form, but alternative liquids or gels may be created. The following provides further description of certain embodiments of the methods and compounds. As described and claimed here, certain terms are defined and used interchangeably.

As used herein, the term "period of time" or "duration of time" means more than a single dosing, application, or administration of the compound. More specifically, these terms mean the compound is administered/applied one or more times per day over a period of seven or more days, wherein generally no two consecutive days pass without the application of the compound and the individual applies the compound at least three or four days in any seven-day period, more preferably four or more days in any seven-day period, more preferably five or more days in any seven-day period, more preferably six or more days in any seven-day period, and most preferably seven consecutive days in any seven-day period. For example, the individual can apply the compound every day, wherein the compound is applied multiple times over the course of the day or the individual may apply the compound a single time in a day.

As used herein, the term "effective amount" or "amount effective to" refers to an amount of the compound required to increase the healing of skin and reduce pain or irritation of the skin. It will be understood by those skilled in the art that a one time, single application of embodiments of the compound may not be effective. Furthermore, it will be understood by those skilled in the art that administering a single dose followed with multiple consecutive days of non-dosing or non-supplementation will not achieve the effective amount as described.

This disclosure provides an important understanding of how the compound may provide healing and relief from pain and irritation when an effective amount is applied to affected areas over a period of time.

In many embodiments, the compound includes ingredients of Lidocaine and *aloe vera*. In some alternatives, the specific species of *Barbadensis* Miller is used for the *aloe vera*. In many alternatives, *Calendula* is used as an ingredient as well. The addition of *Calendula* is thought to be unique, as used in the combination of ingredients in the compound, as it has been studied in relation to radiation burns specifically. Each of the botanicals in the combination of ingredients has a property for skin health and healing. Note that the combination of botanicals provided herein, as well as the percentages of those botanicals, is merely exemplary; and the exact percentages and botanicals used may change and still be within the scope of the compound.

In many alternatives, another unique feature of the compound is that the compound includes a combination of botanicals that serve as a natural preservative. By using the unique combination of preservatives, parabens or other unnatural chemicals are not needed. Furthermore, the combination of botanical preservatives is organic, in the sense of typical FDA standards. This allows the compound to be considered 95% organic, with the 5% Lidocaine being the only non-organic portion.

The compound has a variety of beneficial properties. It is applied like a cream on damaged or irritated areas. The Lidocaine portion of the cream is known to reduce pain. The *aloe vera* and *Calendula* speed healing of various skin injuries and maladies. The *aloe vera* and botanicals may also prevent breakdown of tissue after repeated radiation treatments when used daily during the entire treatment cycle.

In some alternatives, the *aloe vera* is organic *aloe Barbadensis* Miller leaf juice (research has shown that it penetrates to the cellular level and carries the other ingredients deeper into the tissues). Research using *aloe vera* on radiation burns has been conducted since the 1930s. According to dermatological research, *aloe vera* concentrate may help reduce the incidence of skin breakdown, which is associated with repeated radiation treatments. This makes the compound particularly effective at dealing with radiation burns and other radiation-related skin degradation. The compound also may be particularly effective for first-aid kit manufacturers for restaurant and industrial burns, as well as dermatologists for use following dermabrasion treatments.

Many of the embodiments include the use of 4% Lidocaine. Lidocaine is a pain relief ingredient and is optional in all formulations. Typically, pain relief aids in the healing process, since it prevents the patient or user from feeling the need to touch the affected area.

In one embodiment, the compound additionally includes one or more ingredients from the following list:
Glyceryl Stearate (Natural Skin Lubricant)
Stearic Acid (Plant-based Fatty Acid)
*Carthamus Tinctorius* (Safflower) Seed Oil
*Rosa Canina* (Rosehips) Fruit Oil
Sodium Ascorbyl Phosphate (Vitamin C)
*Salvia Sinensis* (Chia) Seed Oil
Vegetable Glycerin Cetyl Alcohol (from Coconut Oil)
Carbomer (Natural Thickener)
*Calendula Officinalis* (Pot Marigold) Flower Extract
*Chamomilla Recutita* (Chamomile) Flower Extract
*Matricaria Chamomilla* (Roman Chamomile) Flower Extract
*Tilia Officinalis* (Linden) Extract
*Hypericum Perforatum* (St. John's Wort) Extract
*Centaurea Cyanus* (Cornflower) Extract
*Vitis Vinifera* (Grape) Seed Extract
*Tabebuia Impetiginosa* (Pau d'Arco) Extract
*Camellia Oleifera* (Japanese Green Tea) Leaf Extract
Tocopheryl Acetate (Vitamin E)

In many embodiments, a natural preservative is used. This natural preservative includes *Leuconostoc*/Radish Root Ferment Filtrate, which functions as a natural preservative. The natural preservative further includes *Lonicera Japonica* (Honeysuckle) Flower Extract, *Lonicera Caprifolium* (Honeysuckle) Extract, and *Populus Tremuloides* (Aspen) Bark Extract. The natural preservative also includes Gluconolactone, which functions as a natural skin conditioner.

Various botanicals have been selected for inclusion in the unique compound. *Chamomilla Recutita* (*Matricaria*) extract is used because it may function as a healing balm to treat burns, wounds, eczema, rashes, anal irritation, and sunburn. It has overall healing and soothing effects.

*Calendula Officinalis* (*Calendula*) flower extract is used because it may function as a soothing anti-inflammatory agent (high content of polysaccharides and terpinoids) and it has antiseptic properties. The resulting compound may be used to treat eczema, burns, wounds, and other types of skin irritations. There are clinical studies that demonstrate that *calendula* can partially prevent some forms of acute dermatitis related to radiation therapy in breast cancer patients. It has been shown to enhance collagen production and aid in preventing excessive scar development. It has a demonstrated ability to increase formation of new blood vessels. Bruises disperse much more quickly with application of this botanical. Last but not least, *calendula* is an immune stimulant.

*Anthemis Nobilis* (Roman Chamomile) flower extract is used because it may function similarly to *Matricaria* in its properties. It is a soothing and calming anti-inflammatory botanical.

Because of its gentle action, *Centaurea Cyanus* (cornflower) flower extract is commonly used around the eyes for its antiseptic properties. Its soothing qualities and emolliency aids in treating aging skin.

*Tilia Cordata* (Linden) flower extract is used because it may have a positive effect on reducing cellulitis and edema. It has been shown to decrease dry skin as well as decrease the dark spots frequently seen on aging skin.

*Hypericum Perforatum* (St. John's Wort) extract is used because of its history of treating bruises, burns, sores, and sprains.

Neuralgia is used because it may have pain relieving activity related to flavonoid content. It has been shown to be active in preventing skin infections. It has strong antiviral activity, decreasing the appearance of cold sores and fever blisters.

*Vitis Vinifera* (Grapeseed) extract is used because it contains high levels of flavonoids and procyanidins. It is a very strong antioxidant and free radical destroyer. It has been shown to strengthen blood vessels and increase circulation with a high content of resveratrol contributing to overall vascular health as well as immune system support.

*Tabebuia Impetiginosa* (Pau d'Arco) extract is used because it may have both anti-fungal and anti-viral properties. It has been used to treat eczema and other forms of dermatitis. It also has been shown to reduce pain and inflammation. It has been reputed to have anti-cancer effects, although the required dosage for this property has side effects.

*Thymus Vulgaris* (Thyme) extract is used because it may have antiseptic, antiviral, and antifungal properties. It has been shown to be effective for bruises and wounds. It has been used to treat cases of crabs and lice, as well as scabies. It is a strong antioxidant.

While there are certain similarities between many of the properties of these botanicals, there is believed to be interaction and possible synergy among them with regard to their remedial potential.

Example of Compound

In one embodiment, the compound may be made according to the following process. The percentage of the total composition is shown in the first column and the named ingredient is listed in the second column. The preparation of the compound is listed as including Phases A-F.

| PHASE A | INCI NAME |
| --- | --- |
| 68.86% Deionized Water | Water |
| 0.17% Ultrez 10 | Carbomer |
| 1.00% Glycerin 99% | Glycerin |

FIG. 1 shows an exemplary method of preparing Phase A of the compound. In step 110, in a mixing tank large enough for the entire batch, deionized water is added. In step 120, slowly add the Ultrez 10 powder and allow it to wet. In step 130, once the Ultrez 10 powder is wetted, add the glycerin and mix slowly until the Ultrez 10 is totally dispersed. In step 140, heat and hold the mixture at 170° F., while preparing Phase B. Cover tank to avoid as much water loss as possible.

| PHASE B | INCI NAME |
| --- | --- |
| 3.00% Glyceryl Stearate | Glyceryl Stearate |
| 3.00% Stearic Acid | Stearic Acid |
| 1.00% Cetyl Alcohol | Cetyl Alcohol |
| 1.50% Hi Oleic Safflower Oil | *Carthamus Tinctorius* (Safflower) Seed Oil |
| 1.00% Rosehip Seed Oil | *Rosa Canina* (Rosehip) Fruit Oil |
| 0.50% Vitamin E | Tocopheryl Acetate |
| 1.00% Chia Seed Oil | *Salvia Sinensis* (Chia) Seed Oil |

Figure 2:
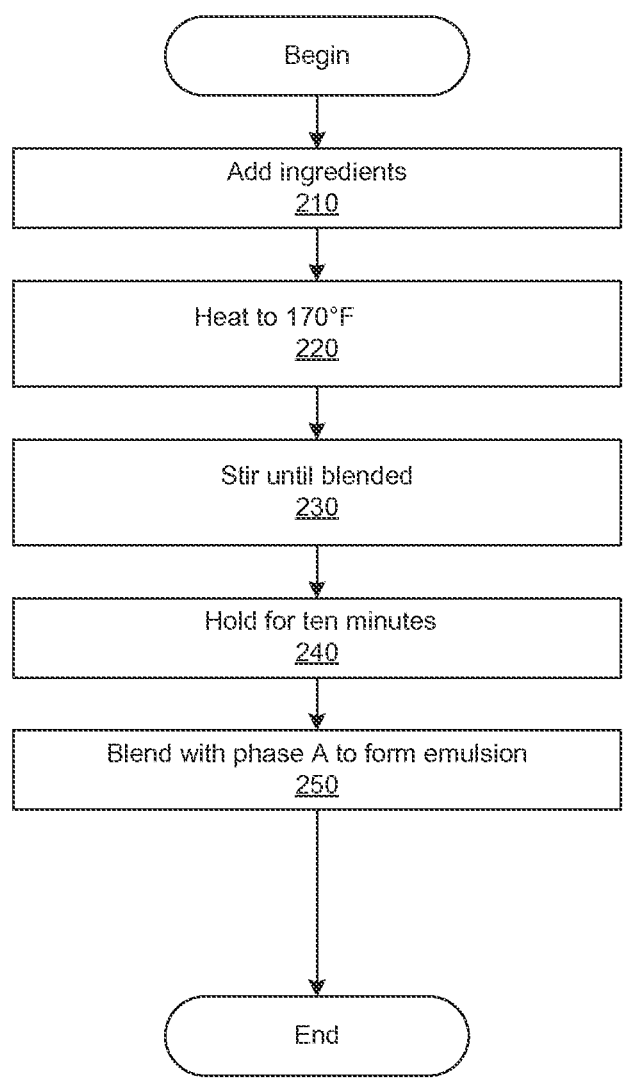
FIG. 2 shows an exemplary method of making Phase B of a compound for intensive skin repair and healing.

FIG. 2 shows an exemplary method of preparing Phase B. In step 210, in a tank large enough for Phase B, add the Phase B ingredients. In step 220, the mixture is heated to 170° F. In step 230, the mixture is stirred and the temperature is held at 170° F. until all ingredients have melted and blended together. In step 240, the mixture is allowed to sit at temperature for an additional ten minutes. In step 250, the mixture is slowly added to Phase A with continued mixing until a smooth, well-blended emulsion has formed and the heat is turned off

| PHASE C (premixed) | INCI NAME |
| --- | --- |
| 3.91% Sodium Hydroxide (10% aqueous solution) | Sodium Hydroxide |

Figure 3:
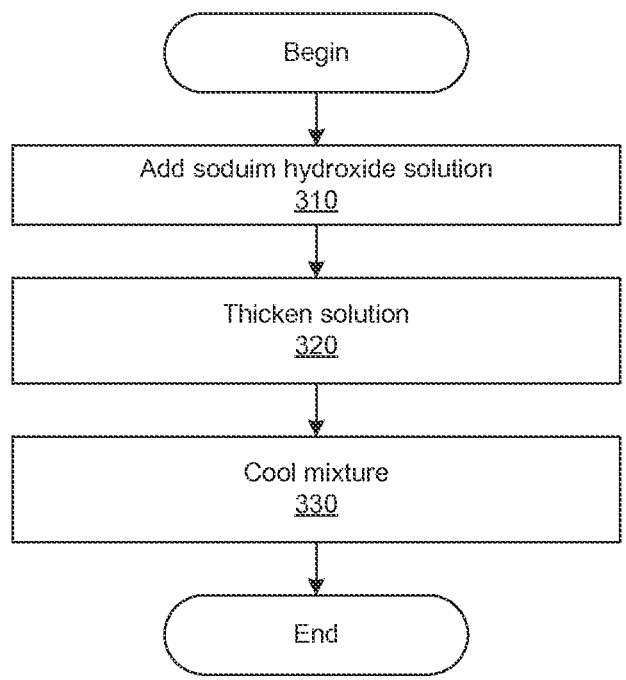
FIG. 3 shows an exemplary method of making Phase C of a compound for intensive skin repair and healing.

FIG. 3 shows an exemplary method of preparing Phase C. In step 310, immediately the sodium hydroxide solution is added to the Phase A and Phase B, while stirring. In step 320, the emulsion should begin to thicken somewhat. Sodium hydroxide solutions are considerably exothermic and are most easily prepared before the rest of the mix is begun. In step 330, the mixtures then is set aside to cool to room temperature and covered until needed. 10% is w/w in this instance. The emulsion must reach 104° F. before the addition of Phase E.

PHASE D (botanical compound)
 0.10% *Chamomilla Recutita* (*Matricaria*) Extract
 0.70% *Calendula Officinalis* (*Calendula*) Flower Extract
 0.10% *Anthemis Nobilis* (Roman Chamomile) Flower Extract
 0.10% *Centaurea Cyanus* (Cornflower) Flower Extract
 0.10% *Tilia Cordata* (Linden) Flower Extract
 0.05% *Hypericum Perforatum* (St. John's Wort) Extract
 0.15% *Vitis Vinifera* (Grapeseed) Extract
 0.10% *Tabebuia Impetiginosa* (Pau d'Arco) Extract
 0.10% *Thymus Vulgaris* (Thyme) Oil Extract In an exemplary embodiment, Phase D includes the above ingredients. To make Phase D, the extracts and mix are combined until an even dispersion is achieved. The combination will make up 1.00% of the entire formula.

| PHASE E | INCI NAME |
|---|---|
| 0.01% Japanese Green Tea Extract | *Camellia Oleifera* Extract |
| 1.00% Vitamin | Sodium Ascorbyl Phosphate |
| 1.55% Organic 200X Aloe Vera Powder | *Aloe Barbadensis* Inner Leaf Juice |
| 5.00% Deionized Water | Water |
| 4.00% Lidocaine Hydrochloride | Lidocaine Hydrochloride |
| 2.00% NataPres Preservative | Leuconostoc/Radish Root Ferment Filtrate, *Lonicera Japonica* (Honeysuckle) Flower Extract, *Lonicera Caprifolium* (Honeysuckle) Extract, *Populus Tremuloides* (Aspen) Bark Extract, and Gluconolactone |

Figure 4:
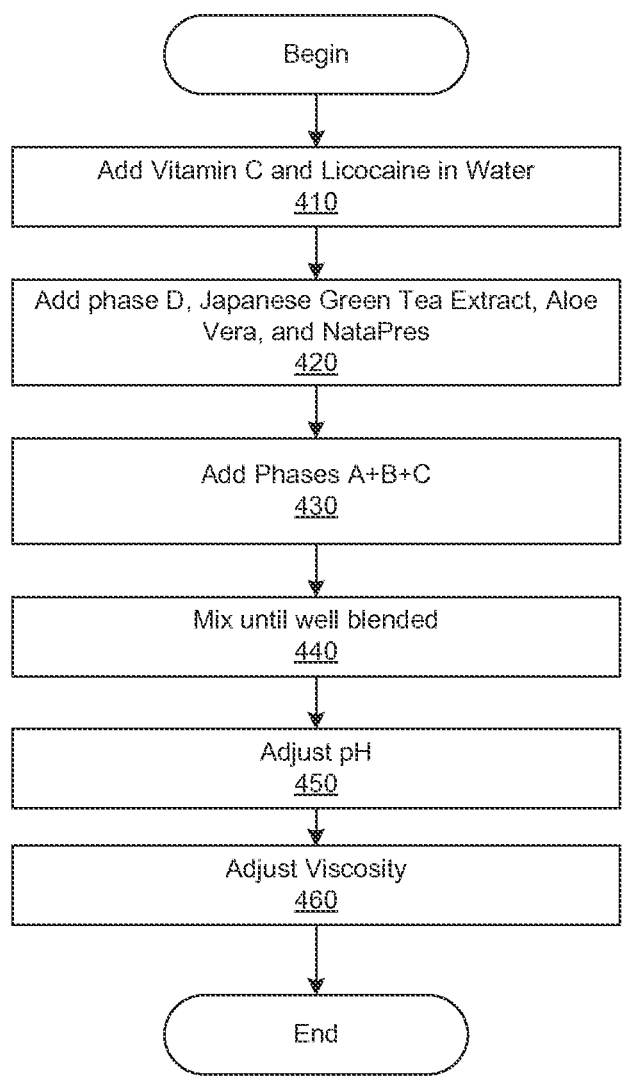
FIG. 4 shows an exemplary method of making Phase E and Phase F of a compound for intensive skin repair and healing.

While Phases A+B+C are cooling, Phase E is prepared. FIG. 4 shows an exemplary embodiment of the process of making Phase E and completing the mixture in Phase F. In step 410, in a separate container large enough for Phase E, Vitamin C and Lidocaine are dissolved in the deionized water. In step 420, after the ingredients are dissolved, the Phase D mixture, Japanese Green Tea Extract, *Aloe Vera* Powder, and NataPres are added. In step 430, the mixture is mixed well until evenly blended. In step 430, once Phases A+B+C have reached a temperature of 104° F., Phase E is slowly added to the A+B+C mixture in the tank. In step 440, the mixture is mixed well for ten minutes or until well blended.

Phase F

Phase F includes quality control procedures for ensuring that the resulting compound is complete. Note that the compound typically is applied in lotion or cream form. In step 450, the pH of the compound is adjusted. To do this, a sample is collected from the finished mixture and taken to the quality control lab for inspection. The pH should be between 6.8 and 7.2. At times, homogenization of the compound may be required. In step 460, the viscosity of the mixture is performed as needed. The viscosity at 25° C. should be between 35,000 and 45,000 centipoise (cps). Timings required for mixing are dependent on the tank, batch size, type of mixer, and speed of mixer.

Although the foregoing description is directed to certain embodiments, it is noted that other variations and modifications will be apparent to those skilled in the art, and may be made without departing from the spirit or scope of the disclosure. Moreover, features described in connection with one embodiment may be used in conjunction with other embodiments, even if not explicitly stated above.

What is claimed is:

1. A skin treatment composition comprising:
 water;
 Ultrez powder;
 glycerin;
 lubricating ingredients;
 sodium hydroxide;
 Vitamin C;
 Lidocaine;
 a Phase D portion of skin-healing botanicals;
 Japanese Green Tea Extract;
 Aloe Vera Powder; and
 natural preservatives.

2. The composition of claim 1, wherein the lubricating ingredient comprises at least one botanical selected from the group consisting of Glyceryl Stearate, Stearic Acid, Cetyl Alcohol, Hi Oleic Safflower Oil, Rosehip Seed Oil, Vitamin E, and Chia Seed Oil.

3. The composition of claim 1, wherein the lubricating ingredient comprises Glyceryl Stearate, Stearic Acid, Cetyl Alcohol, Hi Oleic Safflower Oil, Rosehip Seed Oil, Vitamin E, and Chia Seed Oil.

4. The composition of claim 1, wherein the Phase D portion comprises at least one botanical selected from the group consisting of *Chamomilla Recutita* Extract, *Calendula Officinalis* Flower Ex tract, *Anthemis Nobilis* Flower Extract, *Centaurea Cyanus* Flower Extract, *Tilia Cordata* Flower Extract, *Hypericum* Perforatum Extract, *Vitis Vinifera* Extract, *Tabebuia* Impetiginosa Extract, and *Thymus Vulgaris* Oil Extract.

5. The composition of claim 1, wherein the Phase D portion comprises *Chamomilla Recutita* Extract, *Calendula Officinalis* Flower Extract, *Anthemis Nobilis* Flower Extract, *Centaurea Cyanus* Flower Extract, *Tilia Cordata* Flower Extract, *Hypericum Perforatum* Extract, *Vitis Vinifera* Extract, *Tabebuia lmpetiginosa* Extract, and *Thymus Vulgaris* Oil Extract.

6. The composition of claim 1, wherein the natural preservative comprises *Leuconostoc*/Radish Root Ferment Filtrate, *Lonicera Japonica* Flower Extract, *Lonicera* Caprifolium (Honeysuckle) Extract, *Populus Tremuloides* Bark Extract, and Gluconolactone.

7. The composition of claim 1, wherein the natural preservative comprises at least one botanical selected from the group consisting of *Leuconostoc*/Radish Root Ferment Filtrate, *Lonicera Japonica* Flower Extract, *Lonicera Caprifolium* Extract, *Populus Tremuloides* Bark Extract, and Gluconolactone.

8. The composition of claim 1, wherein a pH of the skin treatment composition is between 6.8 and 7.2.

9. The composition of claim 1, wherein a viscosity of the skin treatment composition is between 35,000 and 45,000 centipoise (cps) at 25° C.

10. A method of treating a skin, comprising applying an effective amount of the composition of claim 1 to the skin.

* * * * *